United States Patent
Yamaguchi et al.

(10) Patent No.: US 6,818,826 B2
(45) Date of Patent: Nov. 16, 2004

(54) FIXING STRUCTURE OF SIGNAL CABLE

(75) Inventors: Takao Yamaguchi, Hachioji (JP); Fujio Sawaguchi, Shirakawa (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/655,335

(22) Filed: Sep. 4, 2003

(65) Prior Publication Data

US 2004/0134677 A1 Jul. 15, 2004

(30) Foreign Application Priority Data

Nov. 22, 2002 (JP) .......................................... 2002-339716

(51) Int. Cl.[7] .................................................. H02R 3/18
(52) U.S. Cl. .................... 174/65 R; 174/135; 174/72 A; 600/110; 439/610
(58) Field of Search ........................... 174/65 R, 65 SS, 174/135, 72 A, 102 C, 104, 100; 439/610, 275, 98; 600/110, 112, 133, 161, 101

(56) References Cited

U.S. PATENT DOCUMENTS

| | | | |
|---|---|---|---|
| 4,919,114 A | * | 4/1990 | Miyazaki .................... 600/110 |
| 5,429,529 A | | 7/1995 | Hashizawa et al. |
| 5,773,759 A | * | 6/1998 | Hablutzel .................. 174/65 R |
| 6,030,339 A | * | 2/2000 | Tatsuno et al. ............. 600/112 |
| 6,080,101 A | * | 6/2000 | Tatsuno et al. ............. 600/112 |
| 6,547,722 B1 | * | 4/2003 | Higuma et al. ............. 600/133 |
| 6,730,849 B2 | * | 5/2004 | Koessler ................... 174/65 R |

FOREIGN PATENT DOCUMENTS

| | | |
|---|---|---|
| JP | 5-293078 | 11/1993 |
| JP | 2000-237128 | 9/2000 |

* cited by examiner

Primary Examiner—Dean A. Reichard
Assistant Examiner—Angel R. Estrada
(74) Attorney, Agent, or Firm—Scully, Scott, Murphy & Presser

(57) ABSTRACT

An outer-coating layer of a signal cable is sandwiched and is fixed between a rear end portion of a cylindrical member and a step portion of the inner diameter of a substrate fixing portion. A slip stop fixes the outer-coating layer in the pull-out direction. An electro-magnetic shielding layer is fixed by a fixing nut and is sandwiched and is fixed between a side end portion of a camera head portion in a pipe member and a step portion of the inner diameter of the cylindrical member.

5 Claims, 7 Drawing Sheets

FIXING STRUCTURE OF SIGNAL CABLE

This application claims benefit of Japanese Application No. 2001-390363 filed in Japan on Dec. 21, 2001, and Japanese Application No. 2002-339716 filed in Japan on Nov. 22, 2002, the contents of which are incorporated by this reference.

BACKGROUND OF THE INVENTION

1. Field of the Invention

The present invention relates to a fixing structure of a signal cable and, more particularly, to a fixing structure of a signal cable of an endoscope apparatus having a feature at the structure of a connector connected to a camera head.

2. Related Art Statement

An outer-coating layer of a cable preferably comprises a material with the inflectivity and softness in view of the operability. A product corresponding to the autoclave sterilization increasingly-uses the outer-coating containing silicon in consideration of the heat resistance. The thickness of the outer-coating layer is made thicker in accordance with the required product specification, giving the priority to the durability, or is made thinner, giving the priority to the outer diameter. However, when the outer-coating layer contains a material which is relatively soft and is easily split, a proper cable fixing method should be selected depending on the situation.

Then, Japanese Unexamined Patent Application Publication No. 5-293078 discloses a method for fixing a cable by fixing a tube member into which the cable is inserted. Further, Japanese Unexamined Patent Application Publication No. 2000-237128 discloses a method for fixing a cable by applying force in the direction for shearing the cable.

OBJECTS AND SUMMARY OF THE INVENTION

The present invention is devised in view of the above situations, and it is an object of the present invention to provide a fixing structure of a signal cable, which is capable of improving the tolerance for pulling out the cable from a main body portion or a connector portion of a probe portion in a medical device irrespective of the thickness of an outer coating when the outer coating contains a relatively soft material.

According to the present invention, a fixing structure of a signal cable comprises: a first tube member for inserting a signal line for transmitting a signal in the signal cable coated sequentially by a conductive shielding layer and a soft outer-coating layer, coated with the shielding layer and intervening between the signal line and the shielding layer; a second tube member having a step portion for forming an inner-diameter portion smaller than an outer diameter of the coated portion of the shielding layer so as to be engaged with the coated portion of the shielding layer which coats the first tube member, intervening between the shielding layer and the outer-coating layer so that the shielding layer can be sandwiched between the first tube member and the step portion; and a third tube member having a projected portion with an inner diameter smaller than an outer diameter of a coated portion of the outer-coating layer so as to be engaged with the coated portion of the outer-coating layer which coats the second tube member, covering the coated portion of the outer-coating layer so that the outer-coating layer can be sandwiched between the second tube member and the projected portion, wherein an end portion of the signal cable is fixed to a predetermined fixed target.

Other features and benefits of the present invention will apparently be understood by the following description.

BRIEF DESCRIPTION OF THE DRAWINGS

FIG. 1 is a diagram showing the structure of an endoscope observation system,

FIG. 2 is a cross-sectional view showing the structure of a connector portion shown in FIG. 1, FIG. 3 is a cross-sectional view showing the cross section of an A—A line shown in FIG. 2, and FIG. 4 is an enlarged view of a substrate fixing member shown in FIG. 2.

FIG. 5 is a cross-sectional view showing a rear end portion of a camera head portion, FIG. 6 is an enlarged view showing a remote switch arranged to a camera head portion shown in FIG. 5, FIG. 7 is a diagram showing the structure of the switch shown in FIG. 6, and FIG. 8 is a diagram of a portion shown by a B arrow in FIG. 7.

DETAILED DESCRIPTION OF THE PREFERRED EMBODIMENTS

First Embodiment (Structure)

Figure 1:
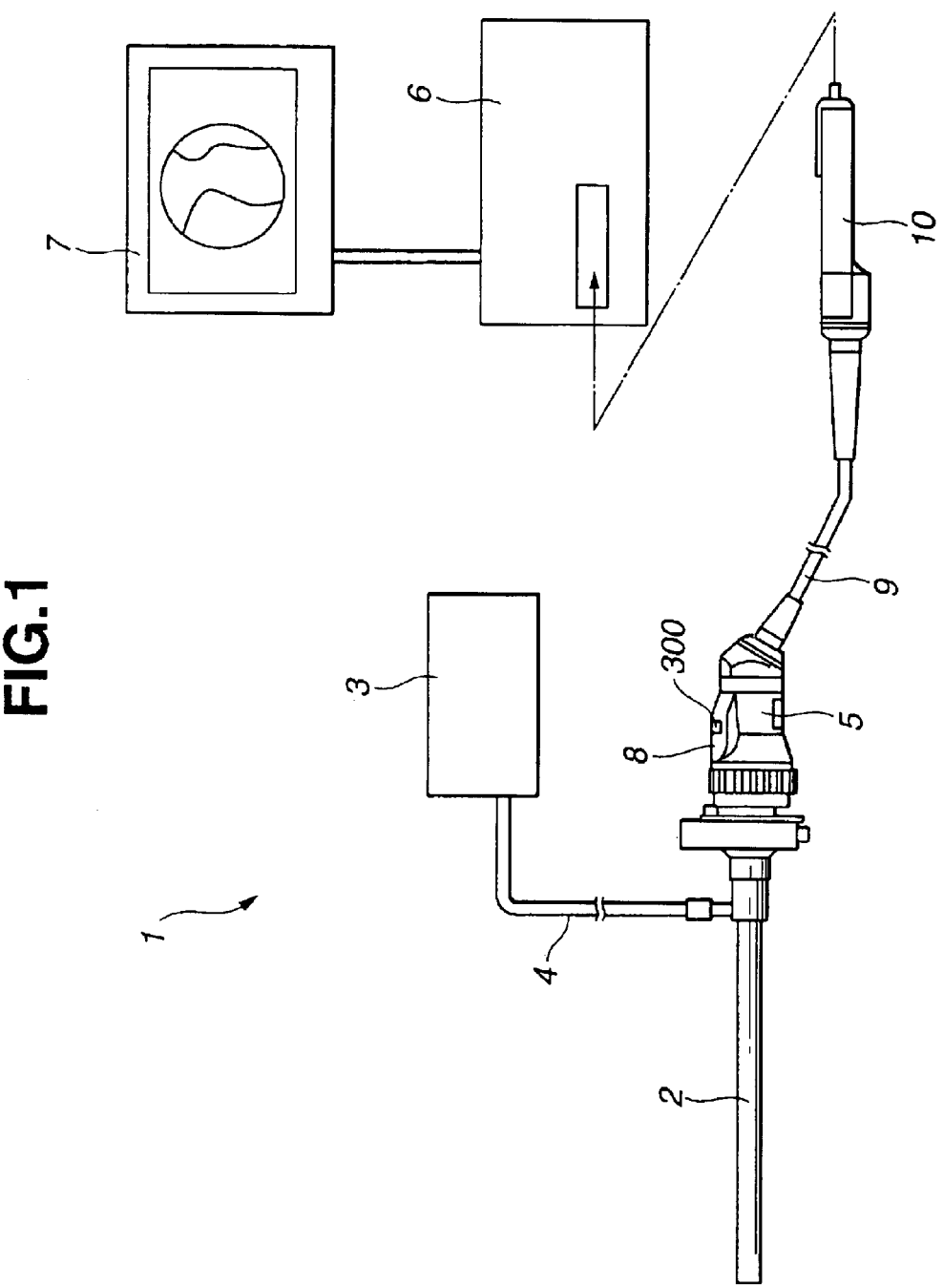
FIGS. 1 to 4 relate to a first embodiment of the present invention.

Referring to FIG. 1, an endoscope observation system 1 includes: an endoscope 2; a light source device 3 which supplies illumination light to the endoscope 2; a light guide cable 4 which connects the endoscope 2 to the light source device 3; an image pick-up device 5 for endoscope which is connected to the endoscope 2 and has a solid-image pick-up device (e.g., a CCD); a video processor 6 which processes a signal from the image pick-up device 5 for endoscope; and a monitor 7 which is connected to the video processor 6 and displays a video signal from the video processor 6.

The image pick-up device 5 for endoscope includes: a camera head portion 8; a signal cable 9; and a connector portion 10.

Figure 2:
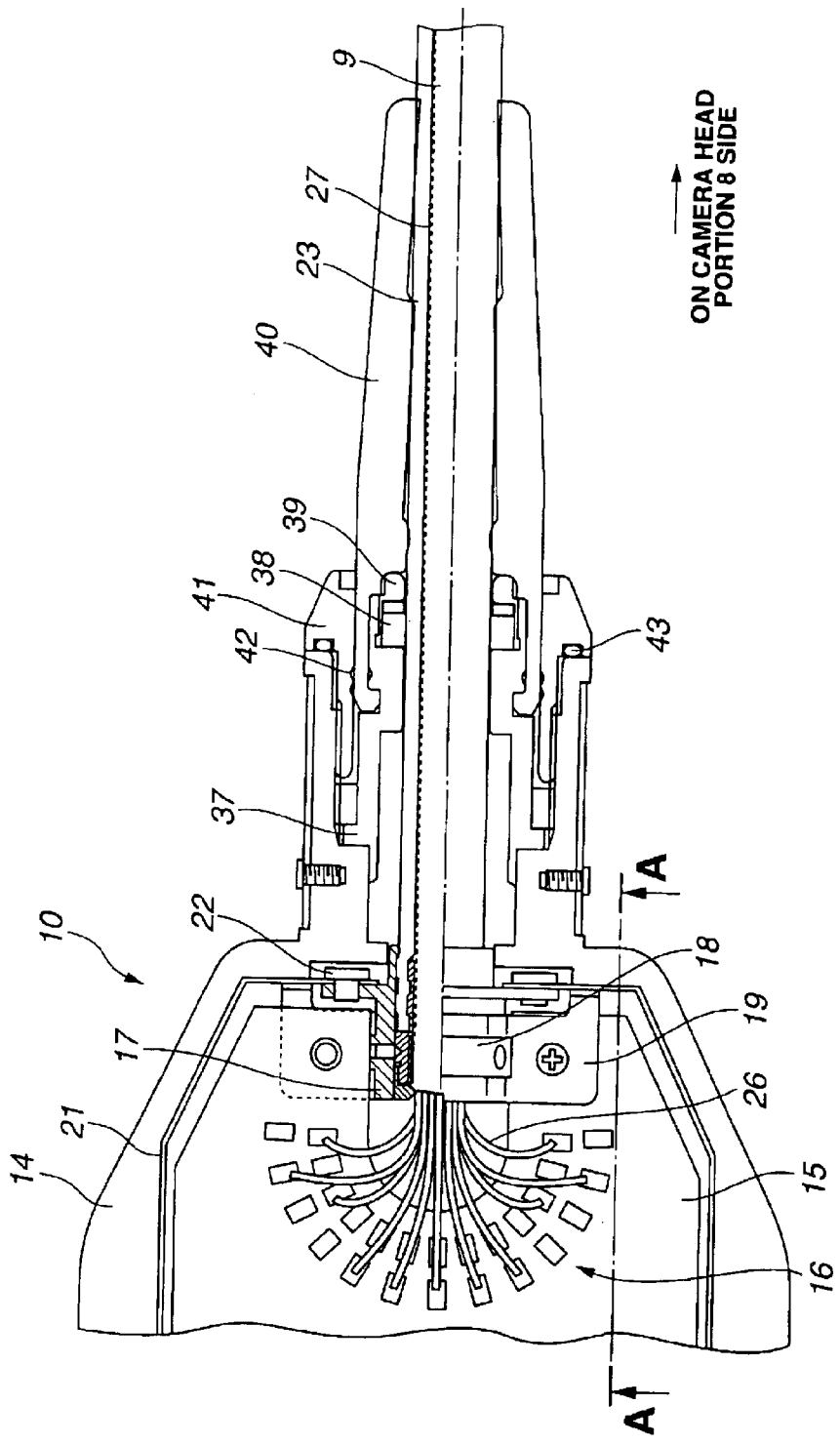
Figure 3:
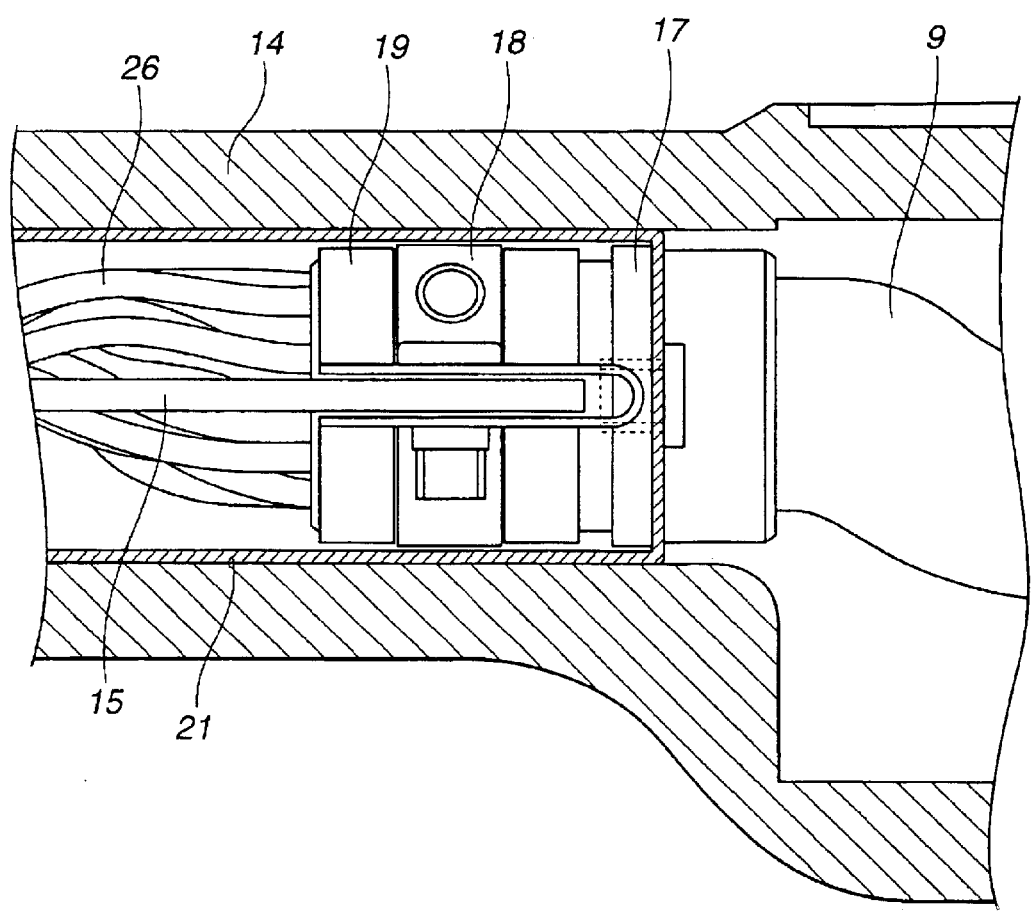

Referring to FIGS. 2 and 3, in the connector portion 10, reference numeral 14 denotes a connector outer-package containing resin. The signal cable 9 is inserted to the camera head portion 8 side of the connector outer-package 14, and a substrate 15 is accommodated on the processor 6 side of the connector outer-package 14.

The signal cable 9 is soldered to a land portion 16 of the substrate 15. The substrate 15 is engaged with a projected portion 18 of a substrate fixing member 17, and is fixed to the substrate fixing member 17 by a press member 19 which is stopped by a screw sandwiching the substrate 15. The substrate fixing member 17 is stopped by a screw 22 to an electro-magnetic shielding case 21 which entirely covers the inner wall of the connector outer-package 14 and is conductive thereto.

A cable inserting hole 24 is arranged to the substrate fixing member 17 and an edge portion of the signal cable 9 is fixed as follows.

Figure 4:
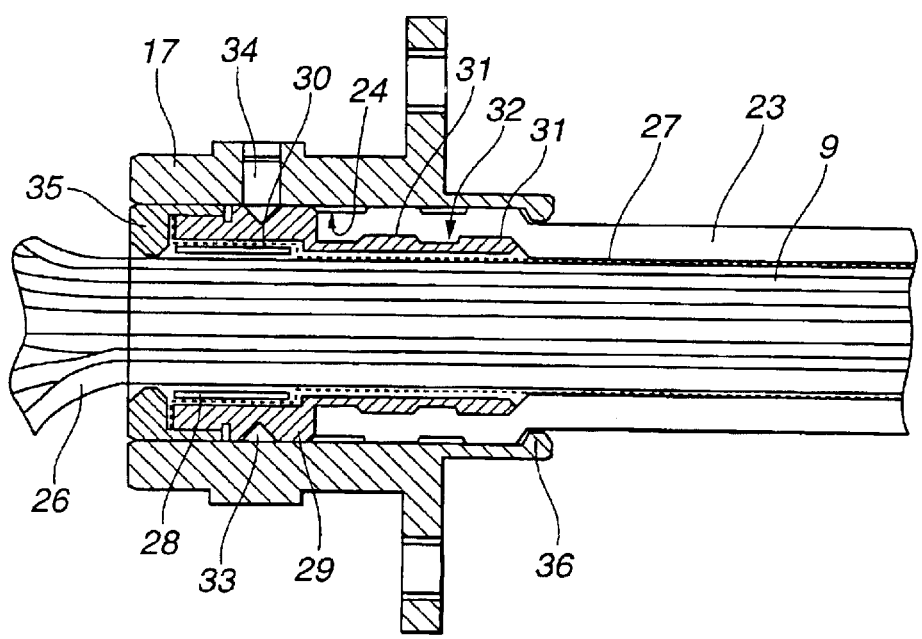
Figure 5:
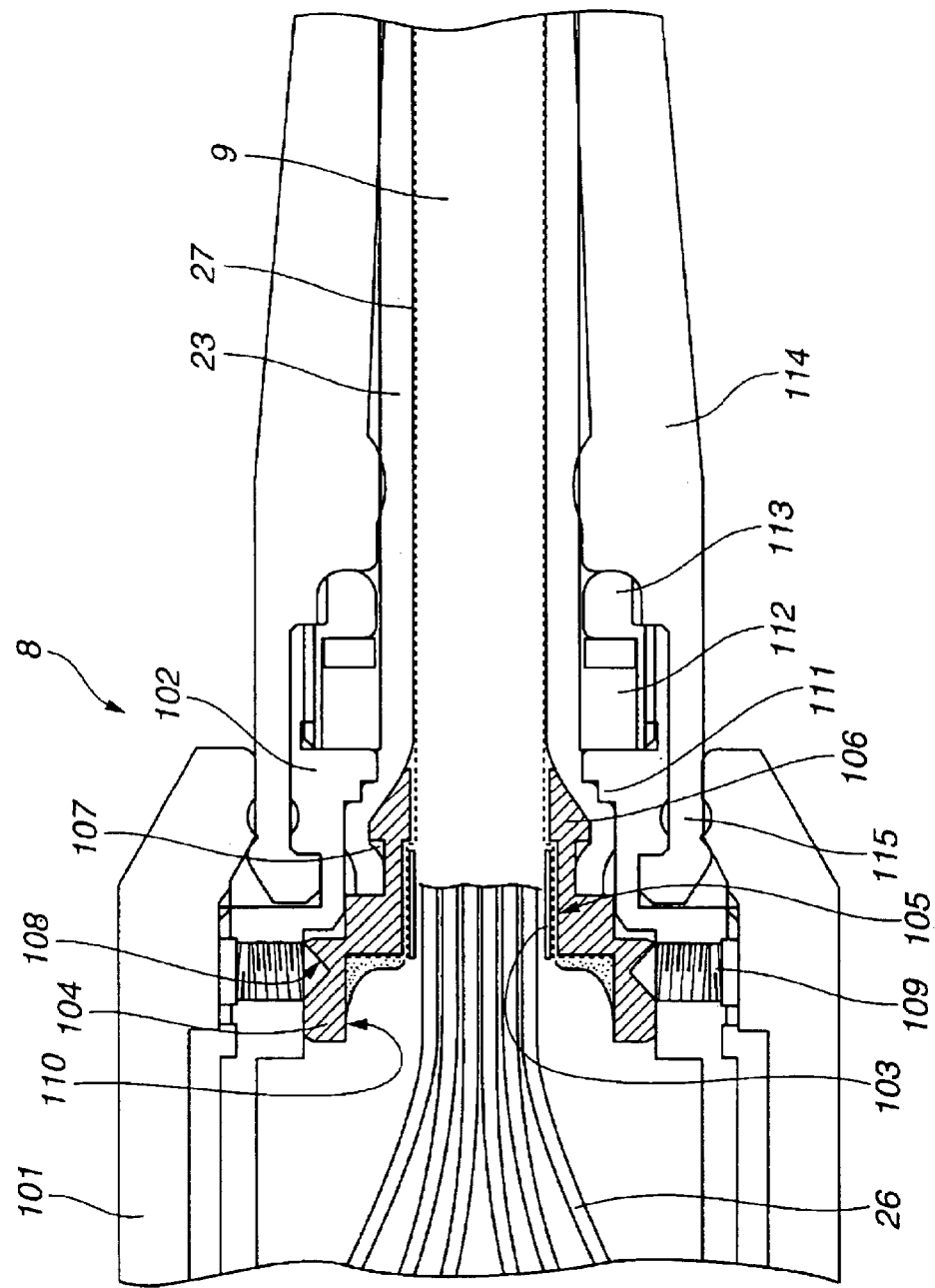
FIGS. 5 to 8 relate to a second embodiment of the present invention.

That is, referring to FIG. 4, a pipe member 28 intervening near a fixing portion of the signal cable 9 is arranged between a signal line 26 and an electro-magnetic shielding layer 27 formed by wiring a metallic material. A cylindrical member 29 intervening near the fixing portion of the signal cable 9 is arranged between the electro-magnetic shielding layer 27 and an outer-package layer 23 containing silicon rubber or PVC.

The cylindrical member 29 has a step portion 30 which accommodates the pipe member 28 coated with the electro-magnetic shielding layer 27 at the inner diameter on the substrate side, and further has a step portion 32 with a slip stopper portion 31 coated with the outer-package layer 23 at the outer diameter on the camera portion 8 side.

A groove 33 having a V-shaped cross-section is formed in the circumferential direction at a part of the outer circumference of the cylindrical member 29 which is fit into the inner diameter of the substrate fixing member 17. A fixing screw 34 having a truncated cone point which is screwed to the substrate fixing member 17 is engaged with the groove 33.

The electro-magnetic shielding layer 27 is widened like a flange along the side end surface of the substrate in the cylindrical member 29, and is fixed by a fixing nut 35. The camera head portion 8 side on the inner circumference of the substrate fixing member 17 has a projected portion 36 having the inner diameter smaller than the outer diameter of a coating portion of the outer-package layer 23 which coats the cylindrical member 29.

The side end portion of the camera head portion 8 in the connector outer-package 20 has a packing 38 for the waterproof of the signal cable 9 and a cylindrical-shaped frame 37 on the whole, and is compressed by a tightening nut 39, thereby tightening the signal cable 9.

A portion 40 for preventing the bending made of rubber which covers and protects the outer circumference of the signal cable 9 is fit into the rear end portion of the frame 37. The nut member 41 screwed to the rear end portion of the connector outer-package 20 compresses and sandwiches a seal portion 42 arranged in the circumferential direction of the portion 40 for preventing the bending. Reference numeral 43 denotes a waterproof packing.

(Operations)

The outer-coating layer 23 is sandwiched and is fixed between a rear end portion of the cylindrical member 29 and a step portion 36 of the inner diameter of the substrate fixing member 17. A slip stop 31 fixes the outer-coating layer 23 in the pull-out direction.

The advance and return of the fixing screw 34 adjusts the amount of force which tightens the outer-coating layer 23 between the rear end portion of the cylindrical member 29 and the projected portion 36.

The electro-magnetic shielding layer 27 is fixed by the fixing nut 35 and is sandwiched and is fixed between a side end portion of the camera head portion 8 in the pipe member 28 and the step portion 30 of the inner diameter of the cylindrical member 29.

Further, the electro-magnetic shielding layer 27 is tightened by the fixing nut 35 and is sandwiched by the pipe member 28, thereby electrically being connected to the cylindrical member 29. The cylindrical member 29 is electrically connected to the substrate fixing member 17 by a fitting surface of the outer circumference thereof and the fixing screw 34, and is conductive to the shielding case 23, thereby forming an electro-magnetic shield of the connector portion 10.

(Advantages)

Although compact, the metallic shielding layer 27 certainly fixes the signal cable 9 and the outer coating is independently fixed. Thus, the strength against the pull out of the signal cable from the connector portion 10 is excessively improved.

Second Embodiment

A second embodiment is substantially the same as the first embodiment and therefore only different portions are described. The same components as those according to the first embodiment are designated by the same reference numerals and are not described.

(Structure)

The signal cable 9 is inserted to the connector side of a camera head outer-package 101 containing resin. A cylindrical-shaped frame 102 containing metal forms an electro-magnetic shield near an image pick-up device (not shown) via metallic members.

Reference numeral 103 denotes a pipe member intervening near a fixing portion of the signal cable 9 between the signal line 26 and the electro-magnetic shield layer 27.

A cylindrical member 104 intervening near the fixing portion of the signal cable 9 is arranged between the outer-coating layer 23 and the electro-magnetic shield layer 27. The cylindrical member 104 includes, at the inner diameter on an edge side thereof, a step portion 105 with a small diameter in which the pipe member 103 is coated with the electro-magnetic shield layer 27 and, at the outer diameter on the rear end side, a step portion 107 coated with the outer-coating layer 23 having a slip stop portion 106.

A groove 108 having a V-shaped cross-section in the circumferential direction is formed at a part of the outer circumference of the cylindrical member 104 which is fit into the inner circumference of the frame 102. A fixing screw 109 screwed to the frame 102, having a truncated cone point, is engaged with the groove 108.

The edge of the electro-magnetic shielding layer 27 is widened like a flange and is soldered along the surface of the step portion 110 of the cylindrical member 104.

The frame 102 has, on the rear end side of the inner circumference thereof, a step portion 111 with the inner diameter smaller than the outer circumference of the coated portion of the outer-coating layer 23 which coats the cylindrical member 104.

Further, the frame 102 has, at the inner circumference of the last end portion thereof, a packing 112 for the waterproof of the signal cable 9 and the frame 102. The packing 112 is compressed by a tightening nut 113, thereby tightening the signal cable 9.

A rubber member 114 for preventing the bending which covers and protects the outer circumference of the signal cable 9 is fit into the outer circumference of the rear end portion of the frame 102. A seal portion 115 is compressed and sandwiched in the circumferential direction at the interval to the rear end portion of the camera head outer-package 101.

Figure 6:
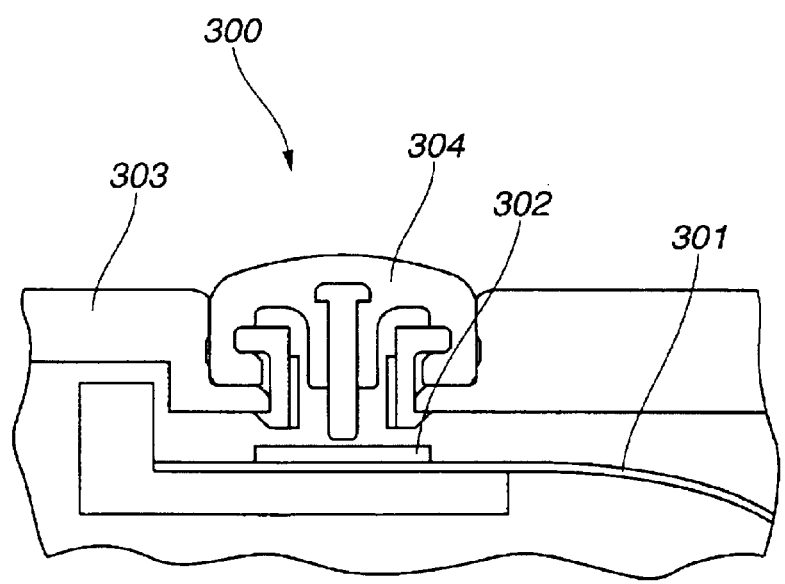

FIG. 6 is an enlarged view of a remote switch 300 (refer to FIG. 1) incorporated in the camera head portion 8.

Referring to FIG. 6, a switch 302 is mounted on a flexible substrate 301 connected to the signal cable 9. A camera head outer-package 303 at the position corresponding to the switch 302 has a button unit 304 for pressing the switch 302.

Figure 7:
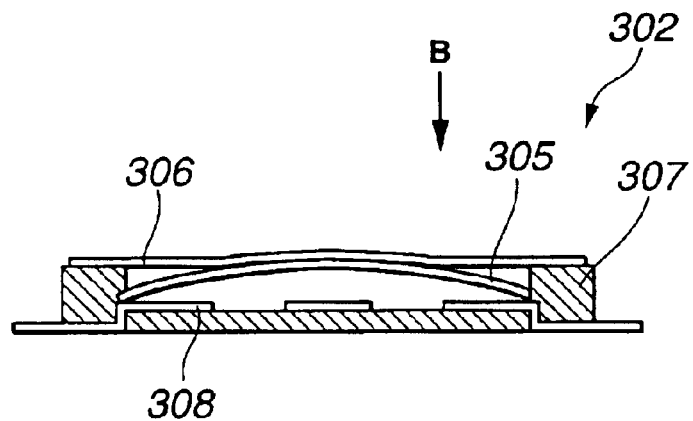
Figure 8:
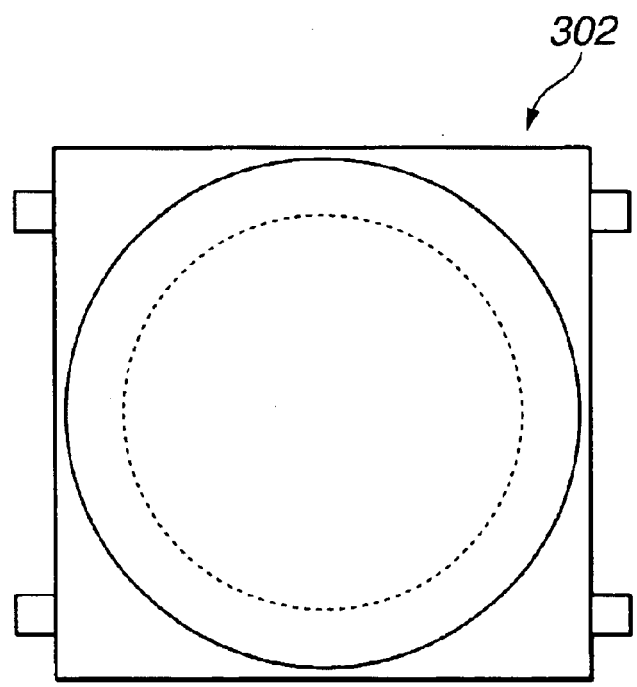

Referring to FIGS. 7 and 8, in the switch 302, a metallic contact base 308 is embedded to a resin body 307. A metallic dome 305 is projected and caved by pressure, thereby turning on/off the switch. The opening of the resin body 303 having the metallic dome 305 is covered by a film 306 with the heat resistance (FIG. 8 is a diagram of a portion shown by a B arrow in FIG. 7).

(Operation)

The soft outer-coating layer 23 containing the rubber is pressed, is sandwiched, and is fixed between the rear end portion of the cylindrical member 104 and the step portion 111 of the inner diameter of the frame 102. The slip stop portion 106 fixes the outer-coating layer 23 in the pull-out direction.

The electro-magnetic shielding layer 27 is fixed to the cylindrical member 104 by soldering, and further is sandwiched and is fixed between the rear end portion of the pipe member 103 and the step portion 105 of the inner diameter of the cylindrical member 104.

The electro-magnetic shielding layer 27 is soldered and is sandwiched by the pipe member 103, thereby electrically being connected to the cylindrical member 104. Further, the electro-magnetic shielding layer 27 is electrically connected to the frame 102 by the fixing screw 109, thus forming the electro-magnetic shield of the camera head portion 8.

In the switch 302, the button unit 304 arranged to the camera head portion is pressed, thereby pressing the metallic dome 305 of the switch 302. Further, insulating portions of the metallic contact base 304 are electrically connected, thereby turning on the switch. A signal of the switch is transmitted to the processor 6 via the signal cable 9. In addition, the film 306 prevents the soldering flux upon mounting from entering the switch 302 and protects the metallic contact from the moisture entering the camera head portion 8.

(Advantage)

The electro-magnetic shielding layer 27 is soldered to the cylindrical member 29 and, therefore, the electro-magnetic shield is conductive without fail.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A fixing structure of a signal cable, comprising:
    a first tube member for inserting a signal line, the signal line transmitting a signal in the signal cable coated sequentially by a conductive shielding layer and a soft outer-coating layer, the first tube member being coated with the shielding layer and intervening between the signal line and the shielding layer;
    a second tube member having a step portion for forming an inner-diameter portion smaller than an outer diameter of the coated portion of the shielding layer so as to be engaged with the coated portion of the shielding layer which coats the first tube member, the second tube member intervening between the shielding layer and the outer-coating layer so that the shielding layer can be sandwiched between the first tube member and the step portion; and
    a third tube member having a projected portion with an inner diameter smaller than an outer diameter of a coated portion of the outer-coating layer so as to be engaged with the coated portion of the outer-coating layer which coats the second tube member, the third tube member covering the coated portion of the outer-coating layer so that the outer-coating layer can be sandwiched between the second tube member and the projected portion,
    wherein an end portion of the signal cable is fixed to a predetermined fixed target.

2. A fixing structure of a signal cable according to claim 1, further comprising:
    a shielding-layer fixing member being fixed to the second tube member and sandwiching an end portion of the shielding layer widened like a flange at an interval to an end surface of the second tube member.

3. A fixing structure of a signal cable according to claim 1, wherein the second tube member is soldered to the shielding layer.

4. A fixing structure of a signal cable according to claim 1, wherein the second tube member has an engaged portion which is engaged with a screw fixed to the third tube member.

5. A fixing structure of a signal cable according to claim 4, wherein the advance and return of the screw adjusts the amount of force which tightens the outer-coating layer between the second tube member and the third tube member.

* * * * *